United States Patent [19]

McKinney et al.

[11] Patent Number: 5,194,657
[45] Date of Patent: Mar. 16, 1993

[54] PROCESS FOR THE PREPARATION OF AMINONITRILES

[75] Inventors: Ronald J. McKinney, Wilmington, Del.; Robert N. McGill, Orange, Tex.

[73] Assignee: E. I. du Pont de Nemours and Company, Wilmington, Del.

[21] Appl. No.: 803,923

[22] Filed: Dec. 9, 1991

Related U.S. Application Data

[63] Continuation-in-part of Ser. No. 637,640, Jan. 4, 1991, abandoned.

[51] Int. Cl.⁵ ............................................. C07C 253/30
[52] U.S. Cl. ................................................... 558/346
[58] Field of Search ......................................... 558/346

[56] References Cited

U.S. PATENT DOCUMENTS

| | | | |
|---|---|---|---|
| 2,205,995 | 6/1940 | Ulrich et al. | 558/346 |
| 3,541,132 | 11/1970 | Knowles | 558/346 |

FOREIGN PATENT DOCUMENTS

| | | |
|---|---|---|
| 1448743 | 7/1966 | France . |
| 54-88220 | 7/1979 | Japan . |
| 1233358 | 5/1971 | United Kingdom . |
| 1464696 | 2/1977 | United Kingdom . |

OTHER PUBLICATIONS

Chemical Abstracts, vol. 105, No. 22, Dec. 1, 1986, Columbus, Ohio; abstract No. 193353k, Z. Vesela et al., "2-amino-2-methylpropionitrile".

*Primary Examiner*—Joseph Paul Brust
*Attorney, Agent, or Firm*—P. Michael Walker

[57] ABSTRACT

A process for preparing an alpha aminonitrile comprises providing a cyclic or acyclic aliphatic ketone in a reactor, adding ammonia to the reactor, mixing the ketone and the ammonia, and adding hydrogen cyanide to the reactor to convert the hydrogen cyanide to an aminonitrile. Preferably, the reactor is purged with ammonia before the addition of hydrogen cyanide. The hydrogen cyanide may be added to the reactor at a constant rate, or it may be added to the reactor at a rate that decreases over time. A portion of the ketone may be added to the reactor during the addition of the hydrogen cyanide to the reactor.

10 Claims, No Drawings

PROCESS FOR THE PREPARATION OF AMINONITRILES

RELATED APPLICATION DATA

This application is a continuation-in-part of application Ser. No. 07/637,640 filed Jan. 4, 1991, now abandoned.

BACKGROUND OF THE INVENTION

1. Field of the Invention

This invention relates to the field of preparing aminonitriles, and more specifically relates to the field of preparing aminonitriles from a ketone, ammonia and hydrogen cyanide.

2. Description of the Related Art

The preparation of aminonitriles by combining, in some manner, the chemical equivalents of a ketone, ammonia, and hydrogen cyanide (HCN) has been performed since Strecker reacted acetone with ammonium cyanide in 1850 to produce acetone aminonitrile. In another process for preparing the acetone aminonitrile, the ammonium cyanide of Strecker is replaced with ammonium chloride and potassium cyanide. The literature is replete with examples of some variation of these procedures that are used to prepare the aminonitriles of various ketones. However, these methods are impractical for commercial operation because the raw materials used in those methods, such as ammonium chloride and potassium cyanide, are much more expensive than other raw materials, such as ammonia and HCN.

A process for preparing an aminonitrile by combining a ketone, ammonia and hydrogen cyanide is disclosed in Czech Patent No. 233,428 which issued on Mar. 14, 1985 to Vesela et al. wherein the aminonitrile is made in a two-step process by first reacting acetone and HCN to form acetone cyanohydrin, and then adding ammonia to the acetone cyanohydrin in an organic solvent. The mixture of acetone cyanohydrin and ammonia in the organic solvent is allowed to sit for two days at room temperature, at which time it produces an 89% yield of acetone aminonitrile.

In a variation of the second step of this two step process, Czech Patent No. 231,245 which issued on Oct. 15, 1984 to Vesela et al. teaches reacting acetone cyanohydrin with ammonia in an autoclave at 65° C. to obtain a 92% yield of acetone aminonitrile.

The general sequence for preparing an aminonitrile from a ketone, ammonia, and hydrogen cyanide in a two step process is illustrated as follows:

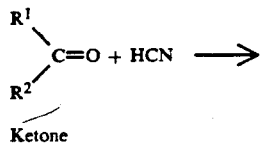
Ketone

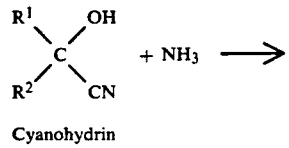
Cyanohydrin

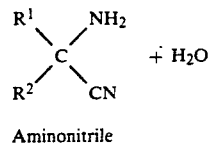
Aminonitrile where the ketone is:
acetone: $R^1=R^2=CH_3-$
methylethylketone: $R^1=CH_3-$ and $R^2=CH_3CH_2-$
methyisobutylketone: $R^1=CH_3-$ and $R^2=(CH_3)_2CHCH-$
cyclohexanone: $R^1$ and $R^2$ together

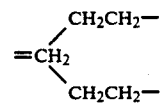

This two step method for preparing an aminonitrile from a ketone, ammonia, and hydrogen cyanide is undesirable for several reasons. First, the process requires an intermediate step, namely the preparation of the cyanohydrin. Secondly, the reaction between the ammonia and the cyanohydrin is very slow, and requires long reaction times. Thirdly, the aminonitrile product obtained from this process includes impurities which may be detrimental in utilizing the aminonitrile in subsequent processes.

SUMMARY OF THE INVENTION

It is an object of this invention to provide a process for the preparation of aminonitriles by the combination of a ketone, ammonia and hydrogen cyanide to convert the ketone to an aminonitrile without the need to prepare a cyanohydrin as an intermediate product.

It is another object of this invention to provide a process for preparing aminonitriles that has shorter reaction times than the prior art.

It is yet another object to provide a process for preparing aminonitriles from a ketone, ammonia and hydrogen cyanide that produces a high yield of an aminonitrile that is high in purity.

It is still another object to provide a process that may be operated in a batch or a continuous mode.

These and other objects of the invention are accomplished by a process for preparing aminonitriles comprising providing a ketone in a reactor, adding ammonia to the reactor, mixing the ketone and the ammonia, and adding hydrogen cyanide to the reactor over a predetermined period of time to convert the hydrogen cyanide to an aminonitrile. This reaction is illustrated as follows.

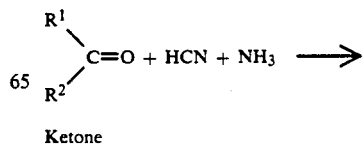
Ketone

-continued

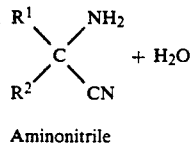

Aminonitrile where the ketone is:
acetone: $R^1=R^2=CH_3-$
methylethylketone: $R^1=CH_3-$ and $R^2=CH_3CH_2-$
methyisobutylketone: $R^1=CH_3-$ and $R^2=(CH_3)_2CHCH-$
cyclohexanone: $R^1$ and $R^2$ together

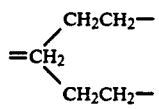

Preferably, the reactor is purged with ammonia before adding the ammonia to remove air and nitrogen from the reactor.

The hydrogen cyanide is contained in a predetermined amount in a reservoir that is pressurized with nitrogen, and is added to the reactor at a constant rate. Optionally, the hydrogen cyanide may be added to the reactor at a rate that decreases over time. The hydrogen cyanide is added to the reactor over a period of time preferably from 2 to 10 hours, and more preferably from 3 to 6 hours.

The pressure of the reactor is maintained from 1 psia to 150 psia (6.9 to 1034 kPa), and preferably from 20 to 65 psia (138 to 448 kPa). The temperature in the reactor is maintained at 0° to 70° C. and preferably from 30° to 50° C.

The molar ratio of hydrogen cyanide to ketone used in the reaction is from 0.9:1 to 1.05:1, and preferably from 0.9:1 to 0.99:1.

A portion of the ketone may be added to the reactor concurrently with the addition of hydrogen cyanide.

Suitable ketones for this process include any cyclic or acyclic aliphatic ketone, such as acetone, methylethylketone, methylisobutylketone or cyclohexanone.

The process may also be operated in a continuous mode wherein the ketone, ammonia, and hydrogen cyanide are continuously added to the reactor. The ammonia is added via a force feed or a flow control mode, with the rate of addition of the ammonia based on the reactor temperature and the feed rates of the ketone and HCN.

DETAILED DESCRIPTION

The present invention relates to a process for preparing an alpha aminonitrile by providing a ketone in a reactor, adding ammonia to the reactor, mixing the ketone and the ammonia, and adding hydrogen cyanide to the reactor over a predetermined period of time to convert the hydrogen cyanide to an aminonitrile. In the alpha form of an aminonitrile, the amine group and the nitrile group are attached to the same carbon atom.

The process takes place in a reactor such as an autoclave. Preferably the autoclave has a stirring mechanism and a means for heating or cooling the interior of the autoclave, such as an internal coil of tubing through which a liquid may be circulated to heat or cool the interior of the autoclave.

In the process, the interior of the autoclave is purged with ammonia gas to remove any air and nitrogen that may be in the autoclave, and then the autoclave is charged with the ketone to be used in the reaction. The ketone is normally present as a liquid.

Ammonia is added to the autoclave, and the ketone and ammonia are mixed prior to the addition of the hydrogen cyanide to the autoclave to promote the conversion of the ketone to the aminonitrile. This mixing is particularly important when the ketone and the ammonia are present in different phases.

During the conversion of the ketone to the aminonitrile, a constant presence of ammonia is maintained in the autoclave, such as by pressurizing the autoclave with ammonia. It is important that an excess of ammonia be present in the reactor to accelerate the reaction and to stabilize the final product. The term "excess of ammonia" means that unreacted ammonia is present in the reactor. Initially, there is no hydrogen cyanide in the reactor to consume the ammonia. As hydrogen cyanide is added to the reactor, however, ammonia is consumed, and additional ammonia must be added to the reactor so that unreacted ammonia is present in the reactor. To be sure an excess of ammonia is present, the pressure of the ammonia in the autoclave is monitored so that when the pressure drops below a certain level, additional ammonia is added to the autoclave to maintain an excess of ammonia. The ammonia may be delivered as a liquid or a gas, with the gaseous form being preferred.

A first reservoir is connected to the autoclave and is charged with a desired amount of hydrogen cyanide. The amount of hydrogen cyanide used is such that the molar ratio of hydrogen cyanide to ketone is from 0.9:1 to 1.05:1, and preferably from 0.9:1 to 0.99:1. It is preferred to have a slight excess of ketone to hydrogen cyanide because excess hydrogen cyanide in the reaction forms by-products and discolors the aminonitrile product.

The hydrogen cyanide may be "inhibited hydrogen cyanide", which means that the hydrogen cyanide is stabilized with a small amount of acid, such a 0.1% sulfuric acid, to prevent the hydrogen cyanide from polymerizing.

The hydrogen cyanide in the reservoir is typically in the form of a liquid, and is pressurized with nitrogen as required so that the contents of the reservoir may be added to the pressurized reactor.

The autoclave is heated to a desired operating temperature, or alternatively, the reaction is started at room temperature and allowed to increase to operating temperature. The operating temperature of the reaction is from 0° to 70° C., and is preferably from 30° to 50° C. The pressure in the reactor is from 1 to 150 psia (6.9 to 1034 kPa), and preferably from 20 to 65 psia (138 to 448 kPa).

The hydrogen cyanide is added to the reactor over a period of time while the temperature is maintained within a desired range by external cooling of the reactor, such as by circulating a cooling liquid through the internal coil of the autoclave. The temperature control is necessary because the reaction is exothermic, and temperatures that are too high will cause the formation of undesirable side products.

Preferably, the HCN is added at a rate such that the concentration of cyanohydrin in the reactor does not exceed 20 mole percent. This results in a shorter overall reaction time and in a higher quality product than if greater than about 20 mole percent cyanohydrin is present.

The rate of addition of the hydrogen cyanide to the autoclave may be kept constant over the period of addition until the hydrogen cyanide is completely expended. Alternatively, the rate of addition of hydrogen cyanide may be adjusted so that the rate decreases over the period of addition. The period of time over which the hydrogen cyanide is added to the reactor may be from ½ hour to several days, preferably from 2 to 10 hours, and more preferably from 3 to 6 hours. Addition times of less than 2 hours are not preferred because such short periods of time produce a product that is inferior in quality.

After the HCN has been added to the autoclave, the reaction is allowed to continue until a desired amount of conversion of the ketone to an aminonitrile has taken place.

The aminonitrile product mixture then is allowed to cool to an ambient temperature in the presence of ammonia. If the autoclave is pressurized, it may be depressurized before or during the cooling of the aminonitrile mixture. The aminonitrile product mixture is stored at an ambient temperature ammonia in the presence of ammonia to increase the stability of the product. The excess ammonia may be recovered and recycled.

The process of the invention may also be carried out by charging only a portion of the total desired amount of ketone to the autoclave. In this case, a second reservoir is connected to the autoclave and is charged with the portion of the total amount of the ketone that is not charged to the autoclave. The second reservoir may be kept under pressure with nitrogen to facilitate the addition of the ketone to the autoclave.

The ketone from the second reservoir is added to the autoclave concurrently with the addition of the hydrogen cyanide to the autoclave.

When the hydrogen cyanide is added to the reactor at a constant rate, the amount of ketone initially charged to the autoclave should be from 15 to 65% of the total amount of ketone to be used in the reaction, and preferably from 30 to 60%. The period of time over which the ketone is added to the autoclave should be no more than 75% of the period of time over which the HCN is added to the autoclave, and preferably from 30 to 60%.

When the HCN is added to the reactor at a rate that decreases over time, the amount of ketone initially charged to the autoclave should be from 15 to 100% of the total amount of ketone to be used in the reaction, and preferably from 25 to 65%. The ratio of the initial rate of HCN addition to the final rate of HCN addition is from 10:1 to 2:1, and preferably from 6:1 to 4:1. The rate of addition of HCN to the reactor should be controlled so that the ketone is added to the autoclave over a period of time equal to or less than the period of time over which the HCN is added. Preferably, the addition of the ketone is complete after 25 to 75% of the HCN has been added, and more preferably after from 40 to 60% of the HCN has been added.

There are at least two advantages to adding part of the ketone to the autoclave at the same time the hydrogen cyanide is added to the autoclave. First, potential by-products arising from the interaction of ammonia and ketone are minimized. Second, the batch time of the reaction is shorter because the addition of HCN may be started before the full charge of ketones present.

It has been found that when hydrogen cyanide is added to an autoclave containing acetone under an ammonia pressure of 65 psia (448 kPa) at 55° C., the conversion to the aminonitrile is completed sooner when the addition time of the hydrogen cyanide is 4 hours than when the addition time is 1 or 2 hours. When the addition time of the hydrogen cyanide is 4 hours, the maximum mole percent of cyanohydrin is only 2%, and the conversion to aminonitrile is complete in another half hour. In contrast, when the addition time of the hydrogen cyanide is 1 hour, the maximum mole percent of unreacted cyanohydrin is 39%, and after a total reaction time of 4½ hours, the mole percent of cyanohydrin is still 10%. When the addition time of the hydrogen cyanide is 2 hours, the maximum mole percent of cyanohydrin is 22%, and after a total reaction time of 4½ hours, the mole percent of unreacted cyanohydrin is still 2.6%.

A measure of the quality of the aminonitrile produced by the inventive process was determined by the color of the product. The color of aminonitriles is an important consideration because color is directly related to the purity of the aminonitrile, and because color is an important feature in some industrial applications.

It is preferred that the color of aminonitriles be water white, which means colorless. Adding hydrogen cyanide to a ketone in the presence of ammonia over a period of time greater than 1 or 2 hours produces aminonitriles that are closer to colorless than aminonitriles prepared by adding hydrogen cyanide over shorter periods of time. The reason for the difference in color is that the color of the aminonitrile and the amount of by-products in the aminonitrile product (which discolor the aminonitriles) are directly related to the concentration of the hydrogen cyanide in the reaction mass, and longer periods of addition of hydrogen cyanide result in a lower overall hydrogen cyanide concentration in the aminonitrile product.

The inventive process may also be operated in a continuous mode. In the continuous mode, ammonia is added to the reactor under a force feed or flow control mode, at a rate based on the reactor temperature and the flow rates of the other reactants. The molar ratio of hydrogen cyanide to ketone is from 0.9:1 to 1.05:1. and preferably from 0.9:1 to 0.99:1. The molar ratio of ammonia to ketone can be from 0.9:1 to 3.0:1. A preferred range is from 1.5:1 to 2.5:1.

The ammonia pressure in the reactor can be lower than in the batch mode without reducing the rate of production of the aminonitrile, with a preferred pressure range being from 5 to 65 psia (34 to 448 kPa). The flow of ammonia minimizes the concentration of inert gases in the reactor by purging the inert gases from the reactor. If inert gases were allowed to build up in the reactor, the aminonitrile reaction would eventually stop because no ammonia would be present to complete the reaction.

The continuous mode uses less ammonia than the batch mode since the reactor is depressurized only when all the product has been made. Therefore, less ammonia is released during the operation, which is desirable because the ammonia released from the reactor must be treated by air pollution control equipment.

EXAMPLES

The following examples were performed by charging all or a part of the ketone to a stirred autoclave which had been purged with ammonia. The pressure of ammonia in the autoclave was then adjusted to a desired level, and the interior of the autoclave was heated to a desired temperature by external heating and cooling, such as by circulating heated liquid through an internal coil of tubing.

The desired pressure of ammonia in the autoclave was maintained by venting or adding ammonia as required. The HCN and remaining ketone, if any, were added to the autoclave from the first and second nitrogen-pressurized reservoirs. In general, a near stoichiometric amount of HCN based on the total amount of ketone was used. The reaction was maintained at the desired temperature by external heating and cooling, such as by circulating hot or cold liquid as required through a coil of tubing inside the reactor. Samples were removed at various times and analyzed by gas chromatography for ketone, cyanohydrin and aminonitrile. In addition to analysis by gas chromatography, the quality of the color of the aminonitrile products produced was determined by assigning relative color quality numbers to the various aminonitrile products in the following way.

The aminonitrile product obtained in Example 4 below was used as a reference product. The aminonitrile product from Example 4 was diluted with various amounts of acetone, with the undiluted product being given an arbitrary color number or value of 2000, and other diluted products being assigned a color number based on the amount of dilution. Other samples of aminonitrile products were compared with acetone dilutions of this reference product to assign a relative color value to those products to evaluate the quality of the aminonitrile products made in the various examples. For example: a 10% solution of the aminonitrile product of Example 4 was assigned a color value of 200, and a 1% solution was given a color number of 20. The lower the color number, the closer the aminonitrile was to colorless. The higher the color number, the darker the color of the aminonitrile.

For color numbers greater than 100, the comparisons were made in capillary tubes. Even with the short path length of capillary tubes, color intensity greater than 2000 could not be distinguished. Colors less than 100 could be distinguished in the original bottles. Samples with a color of less than 1 could not be distinguished from the starting ketone.

EXAMPLE 1

Acetone aminonitrile was prepared as follows. The reactor described above was charged with 3951 parts by weight of acetone, purged with ammonia, pressurized with ammonia to 65 psia, and heated to 50° C. The pressure was maintained at 65 psia (448 kPa) by venting and adding additional ammonia as necessary, and the temperature was maintained at 50° C. by cooling as necessary. HCN (1815 parts, 98.7% of theory based on acetone) was added to the reactor at a constant rate over a period of time of 4 and ¼ hours. At the end of the addition of HCN, 98.7% of the HCN added (as determined by gas chromatography) was converted to acetone aminonitrile, with the remaining 1.3% of HCN present as unreacted acetone cyanohydrin. After an additional ½ hour, the conversion of the HCN to acetone aminonitrile was complete. The color of the acetone aminonitrile on the scale described above was 150.

EXAMPLE 2

Acetone aminonitrile was prepared under the conditions described in Example 1. The reactor was charged with 2878 parts of acetone, and HCN (1283 parts, 95.8% of theory based on acetone) was added to the reactor at a constant rate over a period of time of 1 hour and 50 minutes. At the end of the HCN addition, only 62% of the HCN was converted to acetone aminonitrile, with the remaining 38% of HCN present as cyanohydrin. After the reaction was continued for an additional 2 hours and 20 minutes (total reaction time of 4 hours and 10 minutes), 95.5% of the HCN was converted to aminonitrile and 4.5% of the HCN was still present as unreacted cyanohydrin. The color of the reaction mass on the scale defined above was 350.

EXAMPLE 3

Acetone aminonitrile was prepared under the conditions described in Example 1. The reactor was charged with 3898 parts of acetone, and HCN (1648 parts, 96.4% of theory based on acetone) was added to the reactor over a period of time of 65 minutes. At the end of the HCN addition there was 1.5 times as much cyanohydrin present as aminonitrile. After the reaction was continued for an additional 3 hours and 20 minutes (total reaction time of 4 hours and 25 minutes), 85.3% of the HCN was converted to aminonitrile, with 14.7% of the HCN present as unreacted cyanohydrin. After an additional hour, 92.6% of the HCN was converted to aminonitrile, with 7.3% of the HCN present as unreacted cyanohydrin. At this time the color of the reaction mass on the scale defined above was 900.

EXAMPLE 4

Acetone aminonitrile was prepared under the conditions described in Example 1, except at a temperature of 65° C. The reactor was charged with 3887 parts of acetone, and 1784 parts of HCN (98.6% of the theoretical based on acetone) was added at a constant rate over a period of time of 1 hour. At the end of the addition of HCN, less than half of the HCN had been converted to aminonitrile. After an additional 3 hours there was 4.3% HCN present as unreacted cyanohydrin. After a further hour (total reaction time of 5 hours) there was still 2.1% HCN present as unreacted cyanohydrin. The color of the reaction mass, after the 5 hour reaction cycle, was 2000 on the scale defined above.

EXAMPLE 5

Acetone aminonitrile was prepared under the conditions of Example 1. In this example, only 29% (1200 parts) of the acetone was charged to the reactor. The remaining 2911 parts were charged over a period of time of 3 hours. HCN (1861 parts, 97.2% of theory based on acetone) was charged simultaneously with the acetone but over a 5 hour and 20 minute period. The pressure and temperature were as described in Example 1. After the first 45 minutes no unreacted cyanohydrin could be detected in the reaction mass throughout the remainder of the reaction cycle. The color on the scale described above was 45.

EXAMPLE 6

Acetone aminonitrile was prepared under the conditions described in Example 1. 50% (2079 parts) of the acetone was charged to the reactor. The remaining acetone and 1511 parts of HCN were charged to the reactor simultaneously over a period of time of 2.8 hours. The remaining HCN was then fed to the reactor at reduced rates (477 parts in one hour, followed by 451 parts in 1.4 hours, followed by 153 parts in 0.7 hours). After adding the HCN, the reactor pressure was reduced from 65 psia (448 kPa) to 40 psia (276 kPa) for about 0.5 hours. The reactor pressure was then reduced to 20 psia (138 kPa) and the product pumped to a storage tank where it was stored under an atmosphere of ammonia. Gas chromatographic analysis of the organic constituents of the product were (area %): 98.3% acetone aminonitrile, 1.3% acetone and 0.3% acetone cyanohydrin. The term area percent indicates the area a particular component produced on a gas chromatograph as compared with the total area of product on the gas chromatograph. The color of the product was water white.

EXAMPLE 7

Methylethylketone aminonitrile was prepared using the procedure described in Example 5. The initial charge of methylethylketone was 1700 parts, and an additional 3600 parts of the ketone were added over a period of time of 3 hours. HCN (2016 parts, 94.7% of theory based on the methylethylketone) was added simultaneously with the additional ketone, except that the period of time of the HCN addition was 5 hours. At the end of the addition of the HCN, the conversion of the HCN to aminonitrile was 92.5%, with 7.5% of the HCN present as cyanohydrin. After standing overnight in storage, all the cyanohydrin was converted to aminonitrile. The color on the scale described was 2 at the end of the addition of the reactants.

EXAMPLE 8

Methylethylketone aminonitrile was prepared using the procedure described in Example 6. The reactor was charged with 2650 parts of methylethylketone, and another 2650 parts of methylethylketone and 1134 parts of HCN were added to the reactor simultaneously over a period of 2¼ hours. The remaining HCN was then fed to the reactor at reduced rates as follows: 338 parts over 1 hour, 388 parts over 1½ hours, and then 119 parts over 0.7 hours. The amount of HCN used was 99% of the theoretical stoichiometric amount based upon the total amount of the ketone. The mixture was agitated at temperature and pressure for ½ hour. Gas chromatographic analysis of the organic constituents of the product mix were (area %): 99.2% methylethylketone aminonitrile, 0.4% methylethylketone and 0.4% methylethylketone cyanohydrin. The color of the product was water white.

EXAMPLE 9

Methylisobutylketone aminonitrile was prepared using the procedure described in Example 5. The initial charge of methylisobutylketone was 1820 parts, and an additional 3328 parts of the ketone were added over a period of time of 3½ hours. HCN (1306 parts, 94.1% of theory based on the methylisobutylketone) was added simultaneously with the additional ketone, except that the period of time of the HCN addition was 10 hours. There was no cyanohydrin present at any time during the reaction. The conversion of HCN to aminonirile was essentially 100% at all times. The color of the product on the above described scale was 1.

EXAMPLE 10

Methylisobutylketone aminonitrile was prepared using the method described in Example 6. The reactor was charged with 2650 parts of methylisobutylketone, and then an additional 2650 parts of methylisobutylketone and 730 parts of HCN were added to the reactor over a period of 1.6 hours. The remaining HCN was added to the reactor at reduced rates as follows: 486 parts over 2.0 hours, and then 172 parts over 0.7 hours. The amount of HCN used was 97% of the theoretical stoichiometric amount based upon the total amount of ketone. On standing, the product separated into two liquid phases: an aqueous ammonia lower phase and an organic upper phase. Gas chromatographic analysis of the organic constituents of the organic phase were (area %): 95.9% methylisobutylketone aminonitrile, 3.2% methylisobutylketone and 0.9% methylisobutylketone cyanohydrin. The color of the product was water white.

EXAMPLE 11

Cyclohexanone aminonitrile was prepared using the conditions described in Example 5. The initial charge of cyclohexanone was 1000 parts, and an additional 4203 parts of the ketone were added over a period of time of 2 hours. HCN (1429 parts, 99.6% of theory based on the cyclohexanone) was added simultaneously with the additional ketone, except that the period of time of the of the HCN addition was 4⅔ hours. At the end of the HCN addition the mole ratio of aminonitrile to cyanohydrin was 2.26 to 1. After standing overnight in storage under ammonia, all the cyanohydrin was converted to aminonitrile. The color on the scale described above was 30 at the end of the HCN addition and 60 after overnight storage.

EXAMPLE 12

The following two examples describe continuous production of aminonitrile in a continuous stirred tank reactor (CSTR).

A batch of methylethylketone aminonitrile was prepared in a manner similar to that of Example 6. Fifty percent of the methylethylketone (3184 parts) was charged to the reactor and the reactor was pressurized with ammonia (55 psia, 379 kPa). The remainder of the ketone and 1194 parts of HCN were fed to the reactor over a 3 hour period. The remaining HCN was then fed at reduced rates (694 parts at 398 parts/hour, and then 500 parts at 279 parts/hour). Temperature was maintained between 40° C.-60° C. throughout the operation. After this batch was prepared, the pressure in the reactor was reduced to 32 psia (221 kPa), an overflow line from the reactor to a receiver was opened, and ammonia feed control was changed from pressure control to flow control. Feeds were resumed (methylethylketone, 530 parts/hour; HCN, 187 parts/hour; ammonia, 225 parts/hour) and the temperature and pressure in the reactor were maintained between 35° C.-60° C. and 32 psia, respectively. Steady state conversion, based on the limiting reagent, HCN, was about 97% in the reactor. The remaining 3% conversion occurred in the receiver, which was maintained under 20 psia (138 kPa) ammonia. Gas chromatographic analysis showed the product was 94.1% methylethyl ketone aminonitrile; 4.5% excess methylethylketone; and 0.3% methylethylketone cyanohydrin.

EXAMPLE 13

A batch of acetone aminonitrile was prepared in a manner similar to Example 6. The reactor was then prepared for continuous operation as described in Example 12. Feed rates during continuous operation were: acetone, 692 parts/hour; HCN 316 parts/hour; and ammonia, 260 parts/hour. Steady state conversion, based on HCN, was 99%. Gas chromatographic analysis showed a product of acetone aminonitrile, 98.15%; excess acetone, 1.73%; acetone cyanohydrin, 0.12%.

We claim:

1. An improved process for the preparation of an alpha aminonitrile by providing a ketone in a reactor, adding ammonia to the reactor, and adding hydrogen cyanide to the reactor to convert the hydrogen cyanide to an alpha aminonitrile, said process taking place in the liquid phase, wherein the improvement comprises
   the ketone in the reactor being acetone or methylethylketone,
   providing an amount of hydrogen cyanide to be added to the ketone such that the molar ratio of hydrogen cyanide to ketone is from 0.9:1 to 0.99:1,
   adding the hydrogen cyanide to the reactor over a period of time greater than one hour, and
   maintaining an excess of ammonia in the reactor during the conversion of the hydrogen cyanide to the alpha aminonitrile.

2. A process for the preparation of an alpha aminonitrile by providing a ketone in a reactor, adding ammonia to the reactor, and adding hydrogen cyanide to the reactor to convert the ketone to an alpha aminonitrile, said process taking place in the liquid phase, wherein the improvement comprises
   said ketone in the reactor being acetone, methylethylketone, methylisobutylketone or cyclohexanone,
   providing an amount of hydrogen cyanide to be added to the ketone such that the molar ratio of hydrogen cyanide to ketone is from 0.9:1 to 0.99:1,
   adding the hydrogen cyanide to the reactor at a rate such that the mole percent of cyanohydrin in the reactor is less than 20 percent with respect to the ketone, cyanohydrin and aminonitrile in the reactor, and
   maintaining an excess of ammonia in the reactor during the conversion of the hydrogen cyanide to the alpha aminonitrile.

3. The process of claim 1 further comprising
purging the reactor with ammonia before adding the hydrogen cyanide.

4. The process of claim 1, wherein the hydrogen cyanide is added to the reactor at a constant rate.

5. The process of claim 1, wherein the hydrogen cyanide is added to the reactor at a rate that decreases over time.

6. The process of claim 1, wherein only a portion of the total amount of ketone is charged to the reactor, and the remainder of the total amount of ketone is added to the reactor concurrently with the addition of hydrogen cyanide.

7. The process of claim 6, wherein the amount of ketone initially charged to the reactor is from 15 to 65 weight percent of the total amount of the ketone.

8. The process of claim 6, wherein the period of time over which the ketone is added to the reactor is less than or equal to the period of time over which the hydrogen cyanide is added to the reactor.

9. The process of claim 5, wherein the amount of ketone initially charged to the reactor is from 15 to 99 weight percent of the total amount of the ketone, with the remainder of the ketone being added to the reactor concurrently with the addition of hydrogen cyanide,
   the ratio of the initial rate of addition of hydrogen cyanide to the reactor to the final rate of addition of hydrogen cyanide to the reactor is from 10:1 to 2:1, and
   the rate of addition of hydrogen cyanide to the reactor is controlled so that all of the ketone has been added to the reactor after from 25 to 75 weight percent of the hydrogen cyanide has been added to the reactor.

10. The process of claim 1, wherein the hydrogen cyanide is added to the reactor over a period of from 2 to 10 hours.

* * * * *